United States Patent [19]

Slomka

[11] Patent Number: 5,636,179
[45] Date of Patent: Jun. 3, 1997

[54] SONIC SPECTROMETER AND TREATMENT SYSTEM

[75] Inventor: Bogdan J. Slomka, Ames, Iowa

[73] Assignee: Iowa State University Research Foundation, Ames, Iowa

[21] Appl. No.: 599,194

[22] Filed: Feb. 9, 1996

[51] Int. Cl.⁶ ........................................ G01S 15/00
[52] U.S. Cl. ........................................ 367/95
[58] Field of Search ........................ 367/13, 87, 131, 367/902, 95; 73/1 DV, 579, 599, 620, 627

[56] References Cited

U.S. PATENT DOCUMENTS

| 4,280,557 | 7/1981 | Bodine | 166/177 |
| 5,511,041 | 4/1996 | Michalski | 367/97 |

OTHER PUBLICATIONS

Ultrasonics International Conference and Exhibition programme for Tuesday, Jul. 5, 1995, session entitled: *Resonant Ultrasound Spectroscopy*.

*Primary Examiner*—Daniel T. Pihulic
*Attorney, Agent, or Firm*—Flehr Hohbach Test Albritton & Herbert LLP

[57] ABSTRACT

A novel system and method for treating an object with sonic waveforms. A traveling broad-band sonic waveform containing a broad-band of sonic frequencies is radiated at the object. A traveling reflected sonic waveform containing sonic frequencies reflected by the object is received in response to the traveling broad-band sonic waveform. A traveling transmitted sonic waveform containing sonic frequencies transmitted through the object is also received in response to the traveling broad-band sonic waveform. In a resonance mode, the frequency spectra of the broad-band and reflected sonic waveforms is analyzed so as to select one or more sonic frequencies that cause the object to resonate. An electrical resonance treatment sonic waveform containing the sonic frequencies that cause the object to resonate is then radiated at the object so as to treat the object. In an absorption mode, the frequency spectra of the electrical broad-band, reflected, and transmitted sonic waveforms is compared so as to select one or more sonic frequencies that are absorbed by the object. An electrical absorption treatment sonic waveform containing the sonic frequencies that are absorbed by the object is then radiated at the object so as to treat the object.

24 Claims, 1 Drawing Sheet

5,636,179

SONIC SPECTROMETER AND TREATMENT SYSTEM

The U.S. Government may have certain rights in this invention pursuant to Contract No. W-7405-ENG-82 from the U.S. Department of Energy.

FIELD OF THE INVENTION

The present invention relates generally to systems and methods for treating objects with sonic waves. In particular, it relates to a system and method in which broad-band sonic waveforms are radiated at an object and the frequency spectra of the sonic waveforms reflected by and transmitted through the object are obtained and analyzed to determine the optimum operating frequencies for a given treatment of the object.

BACKGROUND OF THE INVENTION

Systems and methods utilizing sonic waveforms have been used in the past to treat objects for various applications. For example, they have been used to process suspensions of solids in liquids, to mix different fluids, to form emulsions of immiscible liquids, to demulsify immiscible liquids, to comminute solids, etc.

It is known to those skilled in the art that some sonic frequencies are better for certain applications than others. This may be due to the fact that an object may absorb some specific sonic frequencies and may be caused to resonate at others.

Most of the state-of-the-art systems for treating objects with sonic waveforms have fixed single-frequency sonic waveform generators. These systems give a choice of several standard waveforms (e.g., sine, square, triangle, etc.) which are radiated at the object at a single frequency (i.e., radiated at a constant number of wavelength cycles per unit time).

However, other systems have waveform generators which generate sonic waveforms at a range of frequencies. But, none of these systems have the capacity of adjusting the frequencies to suit the particular application for optimum results.

SUMMARY OF THE INVENTION

The foregoing problems are solved by a sonic spectrometer and treatment system and associated method for treating an object with sonic waveforms. The system comprises a waveform generator, one or more sonic transducers, an additional sonic transducer, and a frequency spectrum analyzer.

The waveform generator generates an electrical broad-band sonic waveform containing a broad-band of sonic frequencies. The one or more sonic transducers convert the electrical broad-band sonic waveform to a traveling broad-band sonic waveform and radiate it at the object. The one or more sonic transducers also receive a traveling reflected sonic waveform containing those of the sonic frequencies of the traveling broad-band sonic waveform reflected by the object and convert it to an electrical reflected sonic waveform. The additional sonic transducer receives a traveling transmitted sonic waveform containing those of the sonic frequencies of the traveling broad-band sonic waveform transmitted through the object and converts it to an electrical transmitted sonic waveform.

In a resonance mode, the frequency spectrum analyzer analyzes the sonic frequencies of the electrical broad-band and reflected sonic waveforms and selects therefrom one or more sonic frequencies that cause the object to resonate. The waveform generator generates an electrical resonance treatment sonic waveform containing the selected one or more sonic frequencies that cause the object to resonate. The one or more sonic transducers converting the electrical resonance treatment sonic waveform to a traveling resonance treatment sonic waveform and radiating it at the object so as to treat the object.

In an absorption mode, the frequency spectrum analyzer analyzes the sonic frequencies of the electrical broad-band, reflected, and transmitted sonic waveforms and selects therefrom one or more sonic frequencies that are absorbed by the object. The waveform generator generates an electrical absorption treatment sonic waveform containing the selected one or more sonic frequencies that are absorbed by the object. The one or more sonic transducers convert the electrical absorption treatment sonic waveform to a traveling absorption treatment sonic waveform and radiating it at the object so as to treat the object.

DETAILED DESCRIPTION OF THE INVENTION

Figure 1:
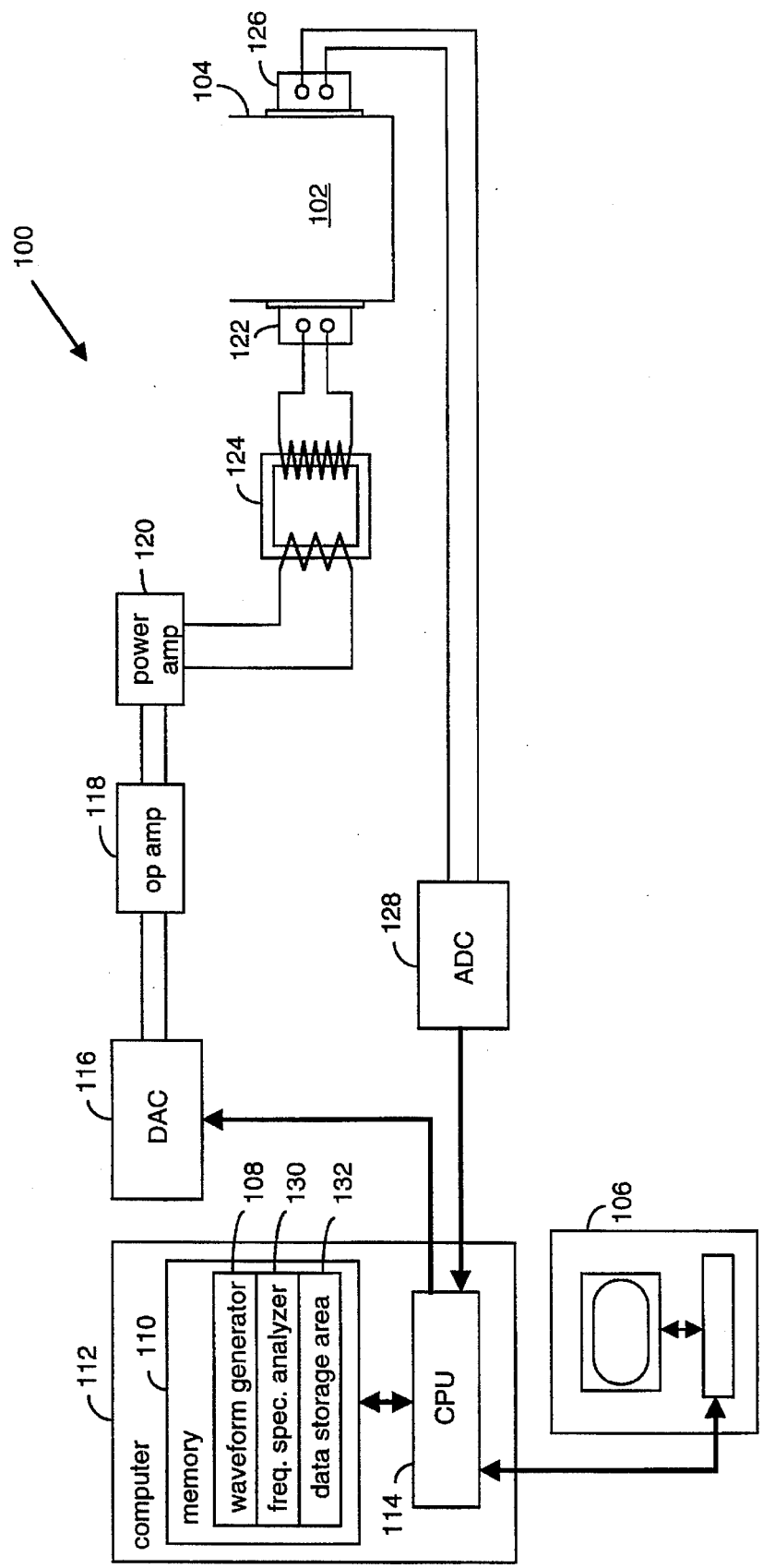
FIG. 1 shows a sonic spectrometer and treatment system for treating an object with sonic waveforms.

Referring to FIG. 1, there is shown a sonic spectrometer and treatment system 100 for treating an object 102 with sonic waveforms for any of the applications discussed earlier. The term sonic is used herein to describe waveforms containing sonic (i.e., 0–20 KHz) and/or ultrasonic frequencies (i.e., 20–1000 KHz).

In the embodiment shown in FIG. 1, object 102 is a fluid and is contained in a treatment tank or container 104. During operation of sonic spectrometer and treatment system 100, a user initiates a command with a user interface 106 to begin treatment of the object.

The command is received by a central processing unit (CPU) 114 of a computer 112 and provided to a waveform generator 108. The waveform generator is stored in a memory 110 of the computer and run on the CPU. In response to the command, the waveform generator generates, as a digital electrical waveform, a diagnostic broad-band sonic waveform pulse containing frequencies in a predetermined broad band or range (e.g., 0–10 KHz).

CPU 114 provides the broad-band sonic waveform pulse to a digital to analog converter (DAC) 116. The DAC converts the broad-band sonic waveform pulse from a digital to an analog electrical waveform.

The broad-band waveform pulse is then provided to an operational amplifier (op amp) 118 and then to a power amplifier (amp) 120. The op amp has sufficient gain (e.g., 4) and the power amp has sufficient power (e.g., 1300 watts) to respectively amplify the voltage and current of the broad-band sonic waveform pulse so that it can be radiated at the object 102 by a transducer 122.

The broad-band sonic waveform pulse is then provided to a transformer based impedance matching circuit 124. The impedance matching circuit insures that there is efficient transfer of power between power amp 120 and transducer 122.

The broad-band sonic waveform pulse is then provided to transducer 122. The transducer is a broad-band sonic transducer (e.g., magnetorestrictive transducer). The transducer is immersed in fluid object 102 and aligned with one wall of treatment tank 104. It converts the broad-band sonic waveform pulse from an analog electrical waveform to a traveling waveform which is radiated in and at the fluid object. Some frequencies of the radiated broad-band wave pulse may be absorbed by object 102, others may be transmitted through the object, and still others may be reflected by the object. Furthermore, even other frequencies may cause the object to resonate.

After the broad-band wave pulse has been radiated at object 102 by transducer 122, if any frequencies of the broad-band wave pulse were reflected by the object, transducer 122 receives a reflected sonic waveform pulse (i.e., echo) containing these reflected frequencies. It then converts this reflected sonic waveform pulse from a traveling waveform to an analog electrical waveform.

In addition, an additional transducer 126 is immersed in fluid object 102 and aligned with the other wall of treatment tank 104 so that it is oppositely located from transducer 122. Like transducer 122, transducer 126 is a broad-band sonic transducer (e.g., magnetorestrictive transducer). If any of the frequencies of the broad-band sonic waveform pulse were transmitted through the object 102, transducer 126 receives a transmitted sonic waveform pulse containing these frequencies. It then converts the transmitted sonic waveform pulse from a traveling waveform to an analog electrical waveform.

The reflected and transmitted sonic waveform pulses are provided to an analog to digital converter (ADC) 128. The ADC converts the reflected and transmitted sonic waveform pulses from analog to digital electrical waveforms.

The reflected and transmitted sonic waveform pulses are then received by CPU 114. A frequency spectrum analyzer 130 is stored in memory 110 and run on CPU 114. It records in data storage area 132 of memory 110 the reflected and transmitted sonic waveform pulses. Additionally, the frequency spectrum analyzer records the broad-band sonic waveform pulse generated by waveform generator 108.

Frequency spectrum analyzer 130 begins analysis in a resonance mode. It does by first computing the Fast Fourier Transforms (FFTs) of the recorded broad-band and reflected waveforms to generate their respective frequency spectra. The frequency spectrum analyzer then compares the computed FFTs of the broad-band and reflected sonic waveform pulses to determine if any frequencies of the frequency spectrum of the reflected sonic waveform pulse are amplified with respect to the same frequencies in the frequency spectrum of the broad-band sonic waveform pulse. If the frequency spectrum analyzer identifies any such frequencies, then these are frequencies at which object 102 resonates. In this case, the frequency spectrum analyzer selects one or more (and up to all) of the identified resonant frequencies as resonance treatment frequencies and generates a frequency spectrum containing the resonance treatment frequencies. It then provides this frequency spectrum to the waveform generator 108.

Waveform generator 108 then computes the Inverse Fast Fourier Transform (IFFT) of this frequency spectrum. As a result, it generates, as a digital electrical waveform, a resonance treatment sonic waveform pulse to be used to treat the object 102 with the resonance treatment frequencies.

Alternatively, if frequency spectrum analyzer 130 determines that there are no resonant frequencies, then it switches to analysis in an absorption mode. In this mode, the frequency spectrum analyzer 130 also computes the FFT of the recorded transmitted sonic waveform to generate its frequency spectrum. It then compares the computed FFTs of the broad-band, reflected, and transmitted sonic waveform pulses to identify any frequencies absorbed by object 102. It does so specifically by subtracting the computed FFTs of the reflected and transmitted sonic waveform pulses from the computed FFT of the broad-band sonic waveform pulse to generate a frequency spectrum of absorbed frequencies. It then selects one or more (and up to all) of the absorbed frequencies and to generate a frequency spectrum that contains the selected frequencies as absorption treatment frequencies. This frequency spectrum is then provided to waveform generator 108 by the frequency spectrum analyzer.

The waveform generator then computes the IFFT of this frequency spectrum to generate, as a digital electrical waveform, an absorption treatment sonic waveform pulse to be used to treat the object 102 with the absorption treatment frequencies.

In both the resonance and absorption modes, the corresponding treatment sonic waveform pulse generated by waveform generator 108 is then converted by DAC 116 from a digital to an analog electrical waveform, amplified by the op and power amps 116 and 118, transferred by the impedance matching circuit 124 from power amp 118 to transducer 122, and radiated by transducer 122 at the object in a similar manner to that described earlier for the broad-band sonic waveform pulse.

As alluded to earlier, the treatment sonic waveform pulse only includes frequencies which were determined earlier to have been absorbed by object 102 (i.e., the absorption treatment frequencies) or to have caused resonance of the object (i.e., the resonance treatment frequencies). As a result, the energy of the treatment sonic waveform pulse is spread out only among these treatment frequencies so that the sonic treatment is efficient. In other words, the object is efficiently treated because energy is not wasted on other frequencies which are not absorbed by or cause resonance of the object.

However, after object 102 has been treated in the manner just described, its resonance or absorption properties may have changed due to the sonic treatment. Therefore, the entire process just described is continuously repeated until the optimum results are achieved.

From the foregoing, those skilled in the art will recognize that sonic spectrometer and treatment system 100 and associated method 200 provide the capacity of adjusting the frequency spectrum of the treatment sonic waveform pulse to suit the particular application for optimum results. In fact, there are numerous other embodiments and applications of sonic spectrometer and treatment system 100 and method 200.

For example, in one embodiment, rather than making the treatment of the object 102 dependent on whether any resonant frequencies are discovered, a user could select operation in either the resonance or absorption modes.

In another embodiment, rather than using transducer 122 to receive the reflected sonic waveform pulse, another transducer, similar to transducer 126, could be used to receive the reflected sonic waveform pulse. In this embodiment, the absorption and resonances modes would still be the same as described earlier.

In still another embodiment, it may not be necessary, convenient, or feasible to use transducer 122 or another transducer, similar to transducer 126, to receive the reflected sonic waveform pulse. In this case, sonic spectrometer and treatment system 100 would not have a resonance mode. Additionally, because waveform generator 108 will only be comparing the frequency spectra of the broad-band and transmitted sonic waveform pulses in the absorption mode, the frequencies it identifies as being absorbed by the object may actually include frequencies that were also reflected by the object. Thus, the absorption treatment sonic waveform pulse may not be as efficient as described earlier because it may contain one or more of these reflected frequencies.

Additionally, in an alternative embodiment to any of the embodiments mentioned earlier, it may not be necessary, convenient, or feasible to position transducer 126 to receive the transmitted sonic waveform pulse. In this embodiment, the resonance mode is the same as that described earlier. However, in the absorption mode, waveform generator 108 will only be comparing the frequency spectra of the broad-band and reflected sonic waveform pulses. Thus, the frequencies it identifies as being absorbed by object 102 may actually include frequencies that were also transmitted through the object. Thus, the absorption treatment sonic waveform pulse may not be as efficient as described earlier because it may contain one or more of these transmitted frequencies.

As a specific application of several of the embodiments just described, sonic spectrometer and treatment system 100 may be used in-situ to prolong and increase production from coal bed demethanation wells. The sonic spectrometer and treatment system would radiate treatment sonic waveform pulses at the coal bed to propagate or create cleats (or fractures) in the coal bed around the wellbore so that the amount of fluid that can be extracted through the coal bed is increased. Additionally, the sonic spectrometer and treatment system would radiate treatment sonic waveform pulses at the coal bed and wellbore to dislodge fine coal particles that clog the cleats in the coal bed from which the fluid is extracted and the perforated portions of the wellbore through which the fluid flows and is filtered.

In this application, a single transducer (similar to transducer 122) is positioned inside the wellbore. To treat the coal bed, the transducer would radiate the broad-band and treatment sonic waveform pulses at the coal bed and receive the reflected sonic waveform pulse from the coal bed. And, it would radiate the broad-band and treatment sonic waveform pulses at the coal bed and receive the reflected sonic waveform pulse from the wellbore to treat the wellbore.

While the present invention has been described with reference to a few specific embodiments, the description is illustrative of the invention and is not to be construed as limiting the invention. For example, in other embodiments of the invention, the Furthermore, various other modifications may occur to those skilled in the art without departing from the true spirit and scope of the invention as defined by the appended claims.

What is claimed is:

1. A system for treating an object with sonic waveforms, the system comprising:

a waveform generator to generate an electrical broad-band sonic waveform containing a broad-band of sonic frequencies;

one or more sonic transducers to convert the electrical broad-band sonic waveform to a traveling broad-band sonic waveform and radiate it at the object and to receive a traveling reflected sonic waveform containing those of the sonic frequencies of the traveling broad-band sonic waveform that are reflected by the object and convert it to an electrical reflected sonic waveform;

a frequency spectrum analyzer to analyze the sonic frequencies of the electrical broad-band and reflected sonic waveforms and to select therefrom one or more sonic frequencies for treating the object;

the waveform generator generating an electrical treatment sonic waveform containing the selected one or more sonic frequencies;

the transducers converting the electrical treatment sonic waveform to a traveling treatment sonic waveform and radiating it at the object so as to treat the object.

2. A system as in claim 1 wherein the selected sonic frequencies comprise one or more sonic frequencies that cause the object to resonate.

3. A system as in claim 1 wherein the selected sonic frequencies comprise one or more sonic frequencies that are absorbed by the object.

4. A system as in claim 1 wherein:

the frequency spectrum analyzer analyzes the sonic frequencies of the electrical broad-band and reflected sonic waveforms and selects the selected one or more sonic frequencies by computing FFTs of the electrical broad-band and reflected sonic waveforms to generate frequency spectra of their sonic frequencies, comparing the generated frequency spectra, selecting the selected one or more sonic frequencies from the compared frequency spectra, and generating a frequency spectrum of the selected one or more sonic frequencies;

the waveform generator generates the electrical treatment sonic waveform by computing an IFFT of the generated frequency spectrum of the selected one or more sonic frequencies.

5. A system as recited in claim 4 wherein:

in a resonance mode:

the frequency spectrum analyzer compares the generated frequency spectra of the electrical broad-band and reflected sonic waveforms by identifying one or more sonic frequencies in the generated frequency spectra of the electrical reflected sonic waveform that are amplified with respect to corresponding one or more frequencies in the generated frequency spectra of the electrical broad-band sonic waveform and cause the object to resonate;

the frequency analyzer selects the selected one or more sonic frequencies from the identified one or more sonic frequencies that cause the object to resonate;

in the absorption mode:

the frequency spectrum analyzer compares the generated frequency spectra of the electrical broad-band and reflected sonic waveforms by subtracting them so as to identify one or more sonic frequencies that are absorbed by the object;

the frequency spectrum analyzer selects the selected one or more sonic frequencies that are absorbed by the object from the identified one or more sonic frequencies that are absorbed by the object.

6. A system for treating an object with sonic waveforms, the system comprising:

a waveform generator to generate an electrical broad-band sonic waveform containing a broad-band of sonic frequencies;

a first sonic transducer to convert the electrical broad-band sonic waveform to a traveling broad-band sonic waveform and radiate it at the object;

a second sonic transducer to receive a traveling transmitted sonic waveform containing those of the sonic frequencies of the traveling broad-band sonic waveform that are transmitted through the object and convert it to an electrical transmitted sonic waveform;

a frequency spectrum analyzer to analyze the sonic frequencies of the electrical broad-band and transmitted sonic waveforms and to select therefrom one or more treatment frequencies for treating the object;

the waveform generator generating an electrical treatment sonic waveform containing the selected one or more frequencies;

the first sonic transducer converting the electrical treatment sonic waveform to a traveling treatment sonic waveform and radiating it at the object so as to treat the object.

7. A system as in claim 6 wherein the selected one or more sonic frequencies comprise one or more sonic frequencies that are absorbed by the object.

8. A system as in claim 6 wherein:

the frequency spectrum analyzer analyzes the sonic frequencies of the electrical broad-band and transmitted sonic waveforms and selects the selected one or more sonic frequencies by computing FFTs of the electrical broad-band and transmitted sonic waveforms to generate frequency spectra of their sonic frequencies, comparing the generated frequency spectra, selecting the selected one or more sonic frequencies from the compared frequency spectra, and generating a frequency spectrum of the selected one or more sonic frequencies;

the waveform generator generates the electrical treatment sonic waveform by computing an IFFT of the generated frequency spectrum of the selected one or more sonic frequencies.

9. A system as in claim 8 wherein:

the frequency spectrum analyzer compares the generated frequency spectra of the electrical broad-band and reflected sonic waveforms by subtracting them so as to identify one or more sonic frequencies that are absorbed by the object;

the frequency spectrum analyzer selects the selected one or more sonic frequencies from the identified one or more sonic frequencies that are absorbed by the object.

10. A system for treating an object with sonic waveforms, the system comprising:

a waveform generator to generate an electrical broad-band sonic waveform containing a broad-band of sonic frequencies;

one or more sonic transducers to convert the electrical broad-band sonic waveform to a traveling broad-band sonic waveform and radiate it at the object and to receive a traveling reflected sonic waveform containing those of the sonic frequencies of the traveling broad-band sonic waveform reflected by the object and convert it to an electrical reflected sonic waveform;

an additional sonic transducer to receive a traveling transmitted sonic waveform containing those of the sonic frequencies of the traveling broad-band sonic waveform transmitted through the object and convert it to an electrical transmitted sonic waveform;

a frequency spectrum analyzer;

in the resonance mode:

the frequency spectrum analyzer analyzing the sonic frequencies of the electrical broad-band and reflected sonic waveforms and selecting therefrom one or more sonic frequencies that cause the object to resonate;

the waveform generator generating an electrical resonance treatment sonic waveform containing the selected one or more sonic frequencies that cause the object to resonate;

the one or more sonic transducers converting the electrical resonance treatment sonic waveform to a traveling resonance treatment sonic waveform and radiating it at the object so as to treat the object;

in the absorption mode:

the frequency spectrum analyzer analyzing the sonic frequencies of the electrical broad-band, reflected, and transmitted sonic waveforms and selecting therefrom one or more sonic frequencies that are absorbed by the object;

the waveform generator generating an electrical absorption treatment sonic waveform containing the selected one or more sonic frequencies that are absorbed by the object;

the one or more sonic transducers converting the electrical absorption treatment sonic waveform to a traveling absorption treatment sonic waveform and radiating it at the object so as to treat the object.

11. A system as in claim 10 wherein:

in the resonance mode:

the frequency spectrum analyzer analyzes the sonic frequencies of the electrical broad-band and reflected sonic waveforms and selects the selected one or more sonic frequencies that cause the object to resonate by computing FFTs of the electrical broad-band and reflected sonic waveforms to generate frequency spectra of their sonic frequencies, compares the generated frequency spectra, selects the selected one or more sonic frequencies that cause the object to resonate from the compared frequency spectra, and generates a frequency spectrum of the selected one or more sonic frequencies that cause the object to resonate;

the waveform generator generates the electrical resonance treatment sonic waveform by computing an IFFT of the frequency spectrum of the selected one or more sonic frequencies that cause the object resonate;

in the absorption mode:

the frequency spectrum analyzer analyzes the sonic frequencies of the electrical broad-band, reflected, and transmitted sonic waveforms and selects the selected one or more sonic frequencies that are absorbed by the object by computing FFTs of the electrical broad-band, reflected, and transmitted sonic waveforms to generate frequency spectra of their sonic frequencies, compares the generated frequency spectra, selects the selected one or more sonic frequencies that are absorbed by the object from the compared frequency spectra, and generates a frequency spectrum of the selected one or more sonic frequencies that are absorbed by the object;

the waveform generator generating the electrical absorption treatment sonic waveform by computing an IFFT of the frequency spectrum of the selected one or more sonic frequencies that are absorbed by the object.

12. A system as recited in claim 11 wherein:

in the resonance mode:

the frequency spectrum analyzer compares the generated frequency spectra of the electrical broad-band and reflected sonic waveforms by identifying one or more sonic frequencies in the generated frequency spectra of the electrical reflected sonic waveform that are amplified with respect to corresponding one or more frequencies in the generated frequency spectra of the electrical broad-band sonic waveform and cause the object to resonate;

the frequency analyzer selects the one or more selected sonic frequencies that cause the object to resonate from the identified one or more sonic frequencies that cause the object to resonate;

in the absorption mode:

the frequency spectrum analyzer compares the generated frequency spectra of the electrical broad-band, reflected, and transmitted sonic waveforms by subtracting them so as to identify one or more sonic frequencies that are absorbed by the object;

the frequency spectrum analyzer selects the selected one or more sonic frequencies that are absorbed by the object from the identified one or more sonic frequencies that are absorbed by the object.

13. A method of treating an object with sonic waveforms, the method comprising the steps of:

generating an electrical broad-band sonic waveform containing broad-band sonic frequencies;

converting the electrical broad-band sonic waveform to a traveling broad-band sonic waveform and radiating it at the object;

receiving a traveling reflected sonic waveform containing those of the sonic frequencies of the traveling broad-band sonic waveform that are reflected by the object and converting it to an electrical reflected sonic waveform;

analyzing the sonic frequencies of the electrical broad-band and reflected sonic waveforms and selecting therefrom one or more sonic frequencies for treating the object;

generating an electrical treatment sonic waveform containing the selected one or more sonic frequencies; and converting the electrical treatment sonic waveform to a traveling treatment sonic waveform and radiating it at the object so as to treat the object.

14. A method as in claim 13 wherein the selected one or more sonic frequencies comprise one or more sonic frequencies that cause the object to resonate.

15. A method as in claim 13 wherein the selected one or more sonic frequencies comprise one or more sonic frequencies that are absorbed by the object.

16. A method as in claim 13 further comprising the steps of:

the analyzing and selecting step comprises:

computing FFTs of the electrical broad-band and reflected sonic waveforms to generate frequency spectra of their sonic frequencies;

comparing the generated frequency spectra;

selecting the one or more selected sonic frequencies from the compared frequency spectra; and generate a frequency spectrum of the selected one or more sonic frequencies;

the electrical treatment sonic waveform generating step comprising computing an IFFT of the frequency spectrum of the selected one sonic frequencies to generate the electrical treatment sonic waveform.

17. A method as recited in claim 16 wherein:

in a resonance mode:

the comparing step comprises generating frequency spectra of the electrical broad-band and reflected sonic waveforms by identifying one or more sonic frequencies in the frequency spectra of the electrical reflected sonic waveform that are amplified with respect to corresponding one or more frequencies in the frequency spectra of the electrical broad-band sonic waveform and cause the object to resonate;

the selecting step including selecting the selected one or more sonic frequencies from the identified one or more sonic frequencies that cause the object to resonate;

in an absorption mode:

the comparing step comprises subtracting the generated frequency spectra of the electrical broad-band and reflected sonic waveforms so as to identify one or more sonic frequencies that are absorbed by the object;

the selecting step comprises selecting the selected one or more sonic frequencies that are absorbed by the object from the identified one or more sonic frequencies that are absorbed by the object.

18. A method for treating an object with sonic waveforms, the method comprising the steps of:

generating an electrical broad-band sonic waveform containing a broad-band of sonic frequencies;

converting the electrical broad-band sonic waveform to a traveling broad-band sonic waveform and radiating it at the object;

receiving a traveling transmitted sonic waveform containing those of the sonic frequencies of the traveling broad-band sonic waveform that are transmitted through the object and converting it to an electrical transmitted sonic waveform;

analyzing the sonic frequencies of the electrical broad-band and transmitted sonic waveforms and selecting therefrom one or more treatment frequencies for treating the object;

generating an electrical treatment sonic waveform containing the selected one or more frequencies; and converting the electrical treatment sonic waveform to a traveling treatment sonic waveform and radiating it at the object so as to treat the object.

19. A method as in claim 18 wherein the selected one or more sonic frequencies comprise one or more sonic frequencies that are absorbed by the object.

20. A method as in claim 18 wherein:

the analyzing and selecting step comprises:

computing FFTs of the electrical broad-band and transmitted sonic waveforms to generate frequency spectra of their sonic frequencies;

comparing the generated frequency spectra;

selecting the selected one or more sonic frequencies from the compared frequency spectra; and generating a frequency spectrum of the selected one or more sonic frequencies;

the electrical treatment sonic waveform generating step comprises computing an IFFT of the generated frequency spectrum of the selected one or more sonic frequencies to generate the electrical treatment sonic waveform.

21. A method as in claim 20 wherein:

the comparing step comprises subtracting the generated frequency spectra of the electrical broad-band and reflected sonic waveforms so as to identify one or more sonic frequencies that are absorbed by the object;

the selecting step comprises selecting the selected one or more sonic frequencies from the identified one or more sonic frequencies that are absorbed by the object.

22. A method of treating an object with sonic waveforms, the method comprising the step of:

generating an electrical broad-band sonic waveform containing a broad-band of sonic frequencies;

converting the electrical broad-band sonic waveform to a traveling broad-band sonic waveform and radiating it at the object;

receiving a traveling reflected sonic waveform containing reflected sonic frequencies comprising those of the broad-band sonic frequencies reflected by the object and converting the traveling reflected sonic waveform to an electrical reflected sonic waveform;

receiving a traveling transmitted sonic waveform containing transmitted sonic frequencies comprising those of the broad-band sonic frequencies transmitted through the object and converting it to an electrical transmitted sonic waveform;

in a resonance mode:
  analyzing the sonic frequencies of the electrical broad-band and reflected sonic waveforms and selecting therefrom one or more sonic frequencies that cause the object to resonate;
  generating an electrical resonance treatment sonic waveform containing the sonic frequencies that cause the object to resonate; and
  converting the electrical resonance treatment sonic waveform to a traveling resonance treatment sonic waveform and radiating it at the object so as to treat the object;

in an absorption mode:
  analyzing the sonic frequencies of the electrical broad-band, reflected, and transmitted sonic waveforms and selecting therefrom one or more sonic frequencies that are absorbed by the object;
  generating an electrical absorption treatment sonic waveform containing the sonic frequencies that are absorbed by the object; and
  converting the electrical absorption treatment sonic waveform to a traveling absorption treatment sonic waveform and radiating it at the object so as to treat the object.

23. A method as in claim 22 wherein:
in the resonance mode:
  the analyzing and selecting step comprising:
    computing FFTs of the electrical broad-band and reflected sonic waveforms to generate frequency spectra of their sonic frequencies, comparing the generated frequency spectra;
    selecting the selected one or more sonic frequencies that cause the object to resonate from the compared frequency spectra; and
    generating a frequency spectrum of the selected one or more sonic frequencies that cause the object to resonate;
  the electrical resonance treatment sonic waveform generating step comprising computing an IFFT of the frequency spectrum of the selected one or more sonic frequencies that cause the object resonate to generate the electrical resonance treatment sonic waveform;

in the absorption mode:
  the analyzing and selecting step comprising:
    computing FFTs of the electrical broad-band, reflected, and transmitted sonic waveforms to generate frequency spectra of their sonic frequencies, comparing the generated frequency spectra;
    selecting the selected one or more sonic frequencies that are absorbed by the object from the compared frequency spectra; and
    generating a frequency spectrum of the selected one or more sonic frequencies that are absorbed by the object;
  the electrical absorption treatment sonic waveform generating step comprising computing an IFFT of the frequency spectrum of the selected one or more sonic frequencies that are absorbed by the object to generate the electrical absorption treatment sonic waveform.

24. A method as recited in claim 23 wherein:
in the resonance mode:
  the comparing step comprises identifying one or more sonic frequencies in the generated frequency spectra of the electrical broad-band waveform that are amplified with respect to corresponding one or more frequencies in the generated frequency spectra of the electrical broad-band sonic waveform and cause the object to resonate;
  the selecting step comprises selecting the one or more selected sonic frequencies that cause the object to resonate from the identified one or more sonic frequencies that cause the object to resonate;

in the absorption mode:
  the comparing step comprises subtracting the generated frequency spectra of the electrical broad-band, reflected, and transmitted sonic waveforms so as to identify one or more sonic frequencies that are absorbed by the object;
  the frequency spectrum analyzer selects the selected one or more sonic frequencies that are absorbed by the object from the identified one or more sonic frequencies that are absorbed by the object.

* * * * *